United States Patent [19]

Uchida et al.

[11] Patent Number: 5,516,436
[45] Date of Patent: May 14, 1996

[54] AGENT FOR TREATING TEXTILE MATERIALS

[75] Inventors: Juji Uchida, Sabae; Masakazu Shimada, Fukui; Takayoshi Kamano, Osaka; Kuniaki Wakita, Kitakatsuragi; Masaaki Okawa, Osaka, all of Japan

[73] Assignee: Nicca Chemical Co., Ltd., Fukui, Japan

[21] Appl. No.: 273,830

[22] Filed: Jul. 12, 1994

[30] Foreign Application Priority Data

Dec. 28, 1993 [JP] Japan ................................ 5-338098

[51] Int. Cl.⁶ .................... C07D 249/18; C07D 413/00; D06M 13/35
[52] U.S. Cl. .......................... 252/8.6; 548/261; 548/260
[58] Field of Search ............................. 252/8.6; 548/261, 548/260

[56] References Cited

U.S. PATENT DOCUMENTS 3,954,706  5/1976  Wang et al. ........................... 548/261

FOREIGN PATENT DOCUMENTS

| 60-59185 | 4/1985 | Japan . |
| 2-41458 | 2/1990 | Japan . |
| 4-91274 | 3/1992 | Japan . |
| 6-192972 | 7/1994 | Japan . |

OTHER PUBLICATIONS

Chemical Abstract 84:35205g, Sep. 20 1975.

*Primary Examiner*—Melissa Bonner
*Attorney, Agent, or Firm*—McAulay Fisher Nissen Goldberg & Kiel

[57] ABSTRACT

An agent for treating textile materials comprising at least one compound selected from the group consisting of compounds of the general formula (I)

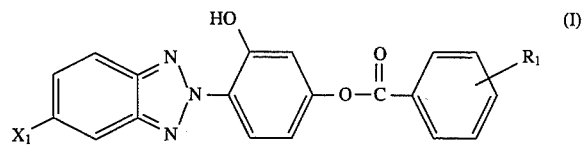

wherein $X_1$ is hydrogen or a halogen, and $R_1$ is hydrogen, a halogen or an alkyl of 1 to 4 carbon atoms, and compounds of the general formula (II)

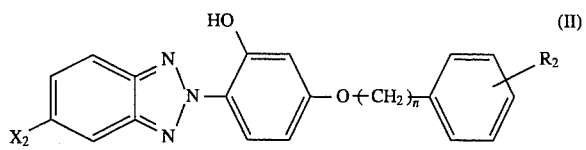

wherein $X_2$ is hydrogen or a halogen, $R_2$ is hydrogen, a halogen or an alkyl of 1 to 4 carbon atoms, and n is an integer of 1 to 3.

3 Claims, No Drawings

AGENT FOR TREATING TEXTILE MATERIALS

BACKGROUND OF THE INVENTION

1. Field of the Invention

The present invention relates to an agent for treating textile materials. The present invention particularly relates to a treating agent capable of improving the light fastness of synthetic textile materials such as polyesters which are degraded or changed in color by light.

2. Description of the Related Art

Those synthetic textile materials which are composed of polyester, nylon, etc., and which are required to have a high degree of durability and light fastness, for example, carpets, car seats, car mats, seat belts, and the like, are generally processed by the use of a dye bath or printing paste, and a light fastness-improving agent in combination. The light fastness is improved, for example, by causing the fibers to adsorb 2-(2'-hydroxy-3'-t-butyl- 5'-methylphenyl)-5-chlorobenzotriazole (Compound I) of the formula

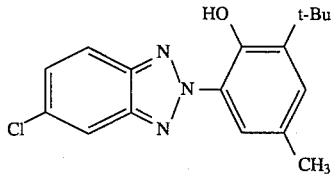

by the use of a dye bath in combination with the aqueous dispersion of Compound I as disclosed in Japanese Unexamined Patent Publication (Kokai) Nos. 60-59185 and 2-41468.

A dyed material obtained by the procedure surely exhibits a fastness rating of 3 to 4 in a light exposure test (irradiation at 83° C. for 200 hours) by a high temperature fadeometer, and the use of the light fastness-improving agent improves the fastness by at least one rating. However, the dyed material is generally subjected to heat setting at 160° to 190° C. after dyeing in practical processing. As a result, Compound I sublimes from fibers when the dyed material has been treated with an aqueous dispersion of Compound I, and there arise problems that the effect of improving the light fastness falls, and that the sublimed material further adheres to the apparatus for heat setting to cause a disadvantage. The dyed material is, therefore, required to be treated at a temperature as low as from 140° to 150° C. at a cost to the setting effect. Accordingly, processing factories are encountering many difficulties in maintaining the productivity and a certain degree of quality of the dyed material. Furthermore, when the dyed material is subjected to such a dry heat treatment at 200° to 210° C. for 2 to 5 minutes as is conducted in the dyeing processing of seat belts, that is, processing by the so-called thermosol method, Compound I sublimes, and the effect of improving the light fastness is completely lost. Furthermore, when a textile material is subjected to processing including printing, for example, processing in which the textile material is pretreated with an aqueous dispersion of Compound I, printed with a printing paste, and fixed by high temperature (HT) steaming at 170° to 180° C. for 7 to 8 minutes, Compound I adsorbed by the pretreated fibers sublimes during the treatment at a high temperature as mentioned above, and the effect of improving the light fastness is almost lost. In addition, even when an aqueous dispersion of Compound I is used in the printing paste in combination, Compound I similarly sublimes during HT steaming, and the effect of improving the light fastness in pattern portions cannot be obtained. Since Compound I itself has a yellow color, it has a disadvantage in that it changes the color shade of a textile material (especially a textile material dyed in a pale color) when used.

Furthermore, the dimming of windowpanes in vehicles has recently become a problem. In those vehicles in which textile materials such as car seats and car mats have been processed with a dispersion of Compound I are used, Compound I gradually sublimes, and there arises a problem that the transparency of the windowpanes in the vehicle is lowered. This is a serious problem from the standpoint of safety, and a quick solution of the problem is desired.

On the other hand, Japanese Unexamined Patent Publication (Kokai) No. 4-91274 discloses that 2-{2'-hydroxy-3'-(3",4",5",6"-tetrahydrophthalimidomethyl)-5'-methylphenyl} benzotriazole (Compound II) of the formula

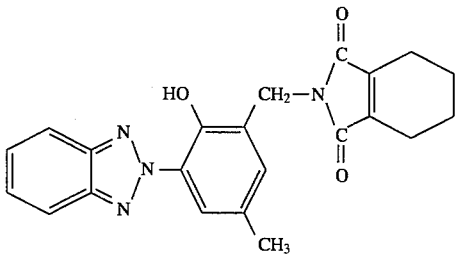

and 2,2'-dihydroxy-4,4'-dimethoxybenzophenone (Compound III) of the formula

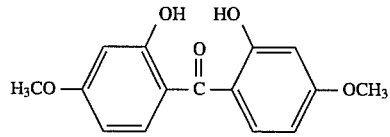

are useful for improving the light fastness of polyester fibers subjected to dyeing operations involving high temperature treatment.

Compound II exhibits a low degree of sublimation and an excellent effect of preventing a decrease in the strength of the fibers caused by light. However, it has drawbacks that its effect of preventing the change in color caused by light is somewhat weak compared with conventional treating agents, and that it exhibits whitening and yellowing caused by optical decomposition of the compound itself in a light fastness test run over a long period of time by exposure using a xenon light source which is said to have a wavelength close to that of the sunlight. Accordingly, Compound II cannot be practically used. Since Compound III itself displays a yellow color to a high degree, textile materials particularly those processed with a pale color dye are discolored. Accordingly, Compound III cannot be used. In addition, when a fiber material is treated with Compound III and dyed simultaneously, Compound III tends to adhere to the body of the dyeing apparatus after the completion of the treatment. As a result, problems such as staining of the processed fabric tend to arise.

Japanese Patent Application No. 4-347028 discloses that 1,4-bis(4-benzoyl-3-oxyphenoxy)butane (Compound IV) of the formula

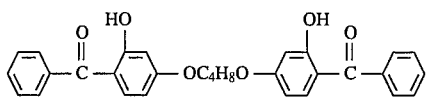

and 2-(2'-hydroxy-4'-methoxyphenyl)-4,6-diphenyl-s-triazine (Compound V) of the formula

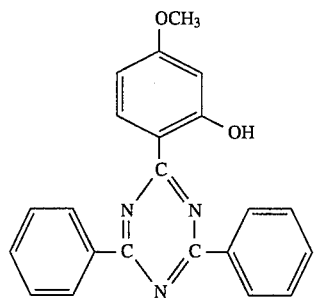

are useful for improving the light fastness of a dyed polyester textile material which is subjected to high temperature treatment. Compounds IV and V surely exhibit a low degree of sublimation, and are excellent in the effect of preventing a decrease in the strength of the fibers caused by light. Moreover, the use of these compounds eliminates such problems as the dimming of windowpanes in vehicles caused by the sublimation of the compounds.

However, these compounds exhibit poor adsorption on cation-dyeable polyester textile materials which are now being used for car seats, etc., and, therefore, do not improve the light fastness of such fibers.

SUMMARY OF THE INVENTION

The present invention is intended to provide an agent for treating textile materials which solves various problems associated with the prior art as described above, which exhibits a low degree of sublimation and excellent adsorption on textile materials, and which improves the light fastness of dyed materials and prevents a decrease in the fiber strength.

To solve the problems as mentioned above, the present invention provides an agent for treating textile materials comprising at least one compound selected from the group consisting of compounds of the general formula (I)

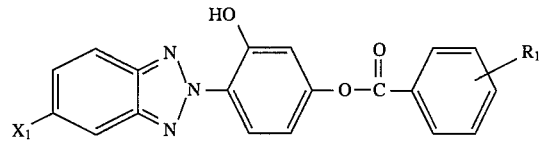

wherein $X_1$ is hydrogen or a halogen, $R_1$ is hydrogen, a halogen or an alkyl of 1 to 4 carbon atoms, and compounds of the general formula (II)

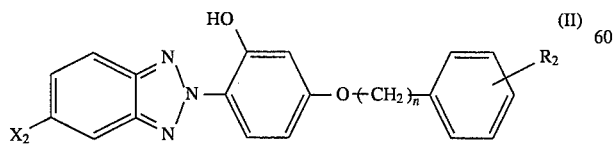

wherein $X_2$ is hydrogen or a halogen, and $R_2$ is hydrogen, a halogen or an alkyl of 1 to 4 carbon atoms, and n is an integer in the range 1 to 3.

DESCRIPTION OF THE PREFERRED EMBODIMENTS

The present inventors have discovered that there can be obtained textile materials exhibiting excellent sublimation resistance of the dye, producing accordingly no dimming of windowpanes in automobiles, etc., and excellent in preventing change in color and degradation caused by light by causing the textile materials to adsorb a treaty agent consisting of at least one of the compounds mentioned above in an amount of 0.01 to 10%, preferably 0.1 to 5%, based on the weight of the fibers.

Examples of textile materials particularly suitable for being treated with the treating agent as mentioned above are woven and knitted fabrics made of synthetic polyester fibers or composite fibers of synthetic polyester fibers and other fibers such as cotton, rayon, wool, nylon and acetate, and raised or napped fabrics therefrom, such as carpets, car mats, car seats and seat belts.

Textile materials may be treated with the treating agents as mentioned above by any procedure such as continuous treatment by padding in an aqueous dispersion, adsorption treatment by immersion, printing treatment and solution treatment with a solvent. However, the treatment of the textile materials is not restricted to those mentioned above. These procedures may be conducted before or after a dyeing step or printing step, or in a dye bath. When textile materials are treated in an aqueous system, the treating agent of the present invention is required to be stably dispersed in water. The treating agent can be dispersed into water by any known method. For example, from 5 to 50% by weight of any of the compounds mentioned above is dispersed into water using an anionic and a nonionic surfactant to form a primary dispersion, and physically ground using a bead mill, etc., to obtain a stabilized aqueous dispersion of fine particles. Although there is no specific limitation on the particle size, the compound is preferably used in pulverized particles having an average particle size of up to 2 μm.

Examples of the useful compounds of the general formula (I) according to the present invention are 2-(2'-hydroxy-4'-benzoyloxyphenyl)-benzotriazole, 2-(2'-hydroxy- 4'-p-methylbenzoyloxyphenyl)-benzotriazole, 2-(2'-hydroxy-4'-p-chlorobenzoyloxyphenyl)-benzotriazole, 2-(2'-hydroxy- 4'-benzoyloxyphenyl)-5-chlorobenzotriazole and 2-(2'-hydroxy- 4'-p-methylbenzoyloxyphenyl)-5-chlorobenzotriazole.

Examples of the compounds of the general formula (II) are 2-(2'-hydroxy-4'-benzyloxyphenyl)-benzotriazole, 2-(2'-hydroxy- 4'-benzyloxyphenyl)-5-chlorobenzotriazole and 2-( 2'-hydroxy-4'-phenethyloxyphenyl)-benzotriazole.

The compounds of the general formula (I) are novel, and can be prepared by reacting a compound of the general formula (III)

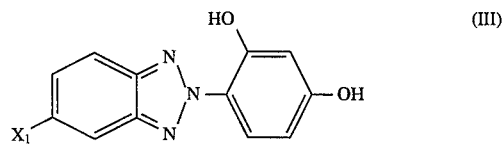

wherein $X_1$ is as defined above, with a compound of the general formula (IV)

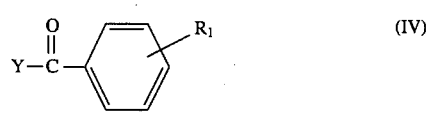

wherein $R_1$ is as defined above, and Y is a hydroxyl, a halogen or an alkoxy of 1 to 3 carbon atoms.

These compounds show a high absorption power at a wavelength of 330 to 350 nm. Compounds showing absorption in such a wavelength range generally tend to show a yellow color. However, the compounds of the present invention are characterized in that they are white crystalline.

The present invention will be explained more in detail by making reference to the following examples.

SYNTHESIS EXAMPLES

In general, an o-nitroaniline is diazotized, and the resultant product is coupled with resorcin by a conventional method to obtain a nitroazo compound. The compound is reduced to give a 2-(2',4'-dihydroxyphenyl)benzotriazole, which is reacted with an esterifying agent to obtain a desired product. Concrete synthesis examples are illustrated below.

Synthesis Example 1

In a reaction vessel were placed 600 ml of toluene, 100 g of 2-(2',4'-dihydroxyphenyl)-2H-benzotriazole, 55 g of benzoic acid and 35 g of phosphorus oxychloride, and the reaction mixture was heated to the refluxing temperature, followed by reacting for 6 hours. The reaction mixture was cooled, washed with hot water, and separated. Crystals were precipitated from the toluene layer, and separated by filtering. The residue was washed with isopropyl alcohol to obtain 105.3 g of white crystals of 2-(2'-hydroxy-4'-benzoyloxyphenyl)benzotriazole.

Synthesis Example 2

In a reaction vessel were placed 600 ml of toluene, 100 g of 2-(2',4'-dihydroxyphenyl)-5-chloro-2H-benzotriazole, 48 g of benzoic acid and 30 g of phosphorus oxychloride, and the mixture was heated to the refluxing temperature, followed by reacting for 6 hours. The reaction mixture was cooled, washed with hot water, and separated. Crystals were precipitated from the toluene layer, and separated by filtering. The residue was washed with isopropyl alcohol to obtain 97.8 g of white crystals of 2-(2'-hydroxy-4'-benzoyloxyphenyl)-5-chlorobenzotriazole.

Table 1 lists for comparison the color shade, melting points, $\lambda_{max}$ and $\epsilon_{max}$ of the compounds obtained in Synthesis Examples 1 and 2, and Compounds I, II and III mentioned above. In addition, $\epsilon_{max}$ represents an absorption strength. A larger value thereof signifies that the absorption strength is higher. Moreover, $\lambda_{max}$ represents the wavelength at which the absorption strength becomes maximum.

TABLE 1

|  | color shade | Melting point (°C.) | λmax | εmax |
| --- | --- | --- | --- | --- |
| Syn. Ex. 1 | white | 172–173 | 336 nm | 24100 |
| Syn. Ex. 2 | white | 185–184 | 343 nm | 26300 |
| Comp. I | pale yellow | 137–141 | 354 nm | 15900 |
| Comp. II | white | 161–166 | 343 nm | 15900 |
| Comp. III | yellow | 130–132 | 339 nm | 10490 |

Note:
Syn. Ex. = Synthesis Example
Comp. = Compound

AQUEOUS DISPERSION EXAMPLES

Examples of methods for dispersing compounds useful for the present invention into water will be illustrated below. In addition, "parts" and "%" in the examples designate "parts by weight" and "% by weight", respectively.

Example 1

A mixture of 150 g of the compound (in powder form) obtained in Synthesis Example 1, 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.40 μm. The particle size was measured using a SALD-1100 (trade name of an apparatus for measuring particle size distribution manufactured by Shimazu Corporation). Measurements of particle size were made in the same manner in the following examples.

Example 2

A mixture of 150 g of the compound (in powder form) obtained in Synthesis Example 2, 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.43 μm.

Example 3

A mixture of 150 g of 2-(2'-hydroxy-4'-benzyloxyphenyl)-benzotriazole (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.43 μm.

Example 4

A mixture of 150 g of 2-(2'-hydroxy-4'-benzyloxyphenyl)- 5-chlorobenzotriazole (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.42 μm.

Comparative Example 1

A mixture of 150 g of Compound I (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.41 μm.

Comparative Example 2

A mixture of 150 g of Compound II (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.41 μm.

Comparative Example 3

A mixture of 150 g of Compound III (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.40 μm.

Comparative Example 4

A mixture of 150 g of Compound IV (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.44 μm.

Comparative Example 5

A mixture of 150 g of Compound V (in powder form), 100 g of Lipotol B-12 (trade name of an anionic surfactant manufactured by Nicca Chemical Co., Ltd.) and 250 g of water was ground in a sand grinder manufactured by Igarashi Kikai Seizo KK for 4 hours to obtain an aqueous dispersion of fine particles having an average particle size of 0.42 μm.

PERFORMANCE EVALUATION TEST EXAMPLES

The aqueous dispersions obtained as described above were used as treating agents, and their performance in treating textile materials was evaluated.

Performance Evaluation Test Example 1

Performance evaluation tests as described below were run using the aqueous dispersions obtained in Examples 1 to 4 and Comparative Examples 1 to 5.

a) Fabrics under test

A raised polyester fabric (weight: 650 g/m$^2$) for a car seat (Fabric 1) and a regular polyester/cation-dyeable polyester (50/50) mixed knitted fabric (Fabric 2) were treated using the method described below, and subjected to a light fastness test and an adsorption test.

b) Method of treatment

The fabrics were treated at 130° C. for 30 minutes under the conditions as described below using a Minicolor dyeing machine (trade name of a dyeing apparatus manufactured by Tekusamu Giken KK), reduction cleaned at 80° C. for 10 minutes, and dried to obtain treated fabrics dyed in a gray color. The fabrics were then dry heat treated at 160° C. for 2 minutes using a pin tenter manufactured by Uenoyama Tekko KK.

| Composition of treatment bath | |
| --- | --- |
| C.I. Disperse Yellow 42 | 0.21% o.w.f. |
| C.I. Disperse Red 302 | 0.08% o.w.f. |
| C.I. Disperse Violet 57 | 0.07% o.w.f. |
| C.I. Disperse Blue 60 | 0.11% o.w.f. |
| C.I. Basic Yellow 67 | 0.11% o.w.f. |
| C.I. Basic Red 29 | 0.15% o.w.f. |
| C.I. Basic Blue 54 | 0.40% o.w.f. |
| Nicca Susolt SD-07 (trade name of a dispersion leveling agent manufactured by Nicca Chemical Co., Ltd.) | 0.5 g/l |
| Acetic acid (90%) | 0.5 g/l |
| Aqueous dispersion of fine particles | 2 or 4% o.w.f. |
| Liquor to goods ratio | 10:1 |
| Composition of reduction cleaning bath | |
| Sunmorl RC-1 (trade name of a soaping agent manufactured by Nicca Chemical Co., Ltd.) | 2 g/l | c) Methods of evaluation (1) Light Fastness

A Method

The treated fabric (backed with a polyurethane 1 cm thick) thus obtained was subjected to light exposure at 83° C. for 400 hours using a high temperature fadeometer manufactured by Suga Shikenki KK. The degree of change in color of the fabric was then judged by the ratings determined in accordance with the color change gray scale standardized by JIS L 0804-74. A dyed fabric having a larger rating exhibits a better light fastness.

B Method

The treated fabric (backed with a polyurethane 1 cm thick) was irradiated by the following procedure using a xenon fadeometer manufactured by Suga Shikenki KK: the fadeometer was operated for 50 cycles (accumulated irradiance: 105000 KJ/m$^2$), each cycle consisting of light exposure at 89° C. for 4.8 hours and placing the fabric in darkness at 38° C. for 1 hour. The degree of change in color of the fabric was then judged by the ratings determined in accordance with the color change gray scale standardized by JIS L 0804-74. A dyed fabric having a larger rating exhibits a better light fastness.

The results thus obtained are shown in Tables 2,3 and 4.

TABLE 2

| | Light fastness (Fabric 1) | | | |
| --- | --- | --- | --- | --- |
| | A method Treatment concentration | | B method Treatment concentration | |
| | 2% | 4% | 2% | 4% |
| Without addition of Aq. disp. of fine particles | 2⁻ | 2⁻ | 2⁻ | 2⁻ |
| Aq. disp. of fine particles in Ex. 1 | 3–4 | 4–5 | 3–4 | 4–5 |
| Aq. disp. of fine particles in Ex. 2 | 3–4 | 4–5 | 3–4 | 4–5 |
| Aq. disp. of fine particles in Ex. 3 | 3–4 | 4–5 | 3–4 | 4–5 |
| Aq. disp. of fine particles in Ex. 4 | 3–4 | 4–5 | 3–4 | 4–5 |
| Aq. disp. of fine particles in Comp. Ex. 1 | 2–3 | 4 | 2–3 | 3–4 |
| Aq. disp. of fine particles in Comp. Ex. 2 | 2–3 | 3 | 2–3 | 2–3 |
| Aq. disp. of fine particles in Comp. Ex. 3 | 3 | 4 | 3 | 4 |
| Aq. disp. of fine particles in Comp. Ex. 4 | 3⁺ | 4–5⁻ | 3⁺ | 4–5⁻ |
| Aq. disp. of fine particles in Comp. Ex. 5 | 3⁺ | 4⁺ | 3 | 4–5⁻ |

Note:
aq. disp. = aqueous dispersion

TABLE 3

| | Light fastness (Fabric 2) A method | | | |
|---|---|---|---|---|
| | Regular portion Treatment concentration | | Cation-dyeable portion Treatment concentration | |
| | 2% | 4% | 2% | 4% |
| Without addition of aq. disp. of fine particles | 2⁻ | 2⁻ | 2⁻ | 2⁻ |
| Aq. disp. of fine particles in Ex. 1 | 3⁺ | 4–5 | 3–4 | 4–5 |
| Aq. disp. of fine particles in Ex. 2 | 3⁺ | 4–5 | 3–4 | 4–5 |
| Aq. disp. of fine particles in Ex. 3 | 3⁺ | 4–5 | 3–4 | 4–5 |
| Aq. disp. of fine particles in Ex. 4 | 3⁺ | 4–5 | 3–4 | 4–5 |
| Aq. disp. of fine particles in Comp. Ex. 1 | 2–3 | 4 | 2–3 | 3–4 |
| Aq. disp. of fine particles in Comp. Ex. 2 | 2–3 | 3 | 2–3 | 3⁻ |
| Aq. disp. of fine particles in Comp. Ex. 3 | 3 | 4 | 3 | 4⁻ |
| Aq. disp. of fine particles in Comp. Ex. 4 | 3⁺ | 4–5⁻ | 3 | 4⁻ |
| Aq. disp. of fine particles in Comp. Ex. 5 | 3⁺ | 4 | 3 | 4⁻ |

Note:
aq. disp. = aqueous dispersion

TABLE 4

| | Light fastness (Fabric 2) B method | | | |
|---|---|---|---|---|
| | Regular portion Treatment concentration | | Cation-dyeable portion Treatment concentration | |
| | 2% | 4% | 2% | 4% |
| Without addition of aq. disp. of fine particles | 2⁻ | 2⁻ | 2⁻ | 2⁻ |
| Aq. disp. of fine particles in Ex. 1 | 3–4 | 4–5 | 3–4 | 4–5 |
| Aq. disp. of fine particles in Ex. 2 | 3–4 | 4–5 | 3–4 | 4–5 |
| Aq. disp. of fine particles in Ex. 3 | 3–4 | 4–5 | 3–4 | 4–5 |
| Aq. disp. of fine particles in Ex. 4 | 3–4 | 4–5 | 3–4 | 4–5 |
| Aq. disp. of fine particles in Comp. Ex. 1 | 2–3 | 3–4 | 2–3 | 3–4 |
| Aq. disp. of fine particles in Comp. Ex. 2 | 2–3 | 3 | 2–3 | 3 |
| Aq. disp. of fine particles in Comp. Ex. 3 | 3 | 4 | 3 | 4⁻ |
| Aq. disp. of fine particles in Comp. Ex. 4 | 3 | 4–5 | 3 | 4⁻ |
| Aq. disp. of fine particles in Comp. Ex. 5 | 3 | 4 | 3 | 4⁻ |

Note:
aq. disp. = aqueous dispersion (2) Judgement of adsorption ratio

The treated fabric thus obtained was extracted with chloroform for 3 hours using a Soxhlet's extractor, and the amount of the compound adsorbed by the fabric was measured. The adsorption ratio was calculated by comparing the measured amount with the amount of the compound in the dyeing solution prepared before dyeing.

Adsorption ratio (%)=[(amount of the extracted compound)/(amount of the compound in the dyeing solution)]×100

The results are shown in Table 5.

TABLE 5

| | Adsorption ratio (%) | | | |
|---|---|---|---|---|
| | Fabric 1 Treatment concentration | | Fabric 2 Treatment concentration | |
| | 2% | 4% | 2% | 4% |
| Without addition of aq. disp. of fine particles | — | — | — | — |
| Aq. disp. of fine particles in Ex. 1 | 99.1 | 98.5 | 98.3 | 98.1 |
| Aq. disp. of fine particles in Ex. 2 | 98.5 | 89.2 | 98.5 | 98.3 |
| Aq. disp. of fine particles in Ex. 3 | 98.3 | 98.6 | 98.5 | 98.5 |
| Aq. disp. of fine particles in Ex. 4 | 98.0 | 98.1 | 98.6 | 98.1 |
| Aq. disp. of fine particles in Comp. Ex. 1 | 88.4 | 98.3 | 98.9 | 98.7 |
| Aq. disp. of fine particles in Comp. Ex. 2 | 98.2 | 98.5 | 97.7 | 97.9 |
| Aq. disp. of fine particles in Comp. Ex. 3 | 98.6 | 98.4 | 97.3 | 98.1 |
| Aq. disp. of fine particles in Comp. Ex. 4 | 89.3 | 91.2 | 81.4 | 64.2 |
| Aq. disp. of fine particles in Comp. Ex. 5 | 93.2 | 88.1 | 78.8 | 60.1 |

Note:
aq. disp. = aqueous dispersion (3) Evaluation of dry heat sublimation tendency The treated fabric was extracted with chloroform for 3 hours before and after dry heat treatment using a Soxhlet's extractor, and the residual ratio of the compound subsequent to dry heat treatment and the amount of the compound adsorbed by the fibers after heat treatment (as the final adsorption ratio) were obtained.

Residual ratio (%)=[(amount of the compound adsorbed subsequent to dry heat treatment)/(amount of the compound adsorbed prior to dry heat treatment)]×100

Final adsorption ratio=[(adsorption ratio)×(residual ratio)]/100

The results thus obtained are shown in Table 6.

TABLE 6

|  | Residual ratio (%) subsequent to dry heat treatment | | Final adsorption ratio (%) | |
|---|---|---|---|---|
|  | Fabric 1 4% treated fabric | Fabric 2 4% treated fabric | Fabric 1 4% treated fabric | Fabric 2 4% treated fabric |
| Without addition of aq. disp. of fine particles | — | — | — | — |
| Aq. disp. of fine particles in Ex. 1 | 95.9 | 96.5 | 94.5 | 94.7 |
| Aq. disp. of fine particles in Ex. 2 | 94.6 | 95.9 | 92.8 | 94.1 |
| Aq. disp. of fine particles in Ex. 3 | 94.9 | 97.0 | 93.6 | 95.5 |
| Aq. disp. of fine particles in Ex. 4 | 95.2 | 96.5 | 93.4 | 94.7 |
| Aq. disp. of fine particles in Comp. Ex. 1 | 73.1 | 71.4 | 71.9 | 70.1 |
| Aq. disp. of fine particles in Comp. Ex. 2 | 91.8 | 93.1 | 90.4 | 91.1 |
| Aq. disp. of fine particles in Comp. Ex. 3 | 90.7 | 89.0 | 89.2 | 96.1 |
| Aq. disp. of fine particles in Comp. Ex. 4 | 95.1 | 96.3 | 86.7 | 61.8 |
| Aq. disp. of fine particles in Comp. Ex. 5 | 95.4 | 96.2 | 84.0 | 57.8 |

Note:
aq. disp. = aqueous dispersion

It is seen from these results that the treating agents of the present invention are excellent in adsorption on polyester textile materials, especially cation-dyeable polyester textile materials, and that the treated materials are excellent in light fastness.

Performance Evaluation Test Example 2

Performance evaluation tests as described below were run using the same aqueous dispersions as mentioned above.

a) Fabric under test

The gray raised polyester fabric (weight: 650 g/m$^2$) for a car seat having been subjected to dyeing treatment in Performance Evaluation Test Example 1 was printed by the method as described below, and subjected to a light fastness test.

b) Method of Treatment

The fabric under test was printed with a colored paste having a composition as described below using an autoscreen printing test apparatus having a #1500 mesh screen and manufactured by Tsujii Senki KK. The printed fabric was dried at 100° C. for 1 minute, subjected to fixing treatment at 175° C. for 7 minutes using a HT steamer manufactured by Tsujii Senki KK, reduction cleaned, and dried.

| Composition of colored paste for printing | |
|---|---|
| Nicca Gum 2A (trade name of a modified starch size manufactured by Nicca Chemical Co., Ltd.) containing 10% water | 150 g |
| Nicca Gum C-170 (trade name of a CMC size manufactured by Nicca Chemical Co., Ltd.) containing 8% water | 450 g |
| C.I. Disperse Blue 60 | 10 g |
| Sunflowren FK-2 (trade name of a dye build-up enhancing agent for printing manufactured by Nicca Chemical Co., Ltd.) | 30 g |
| Citric acid | 2 g |
| Sodium chlorite | 1 g |
| Aqueous dispersion of fine particles | 20 g |
| Water | 337 g |
| Total | 1000 g |

| Composition of reduction cleaning bath | |
|---|---|
| Sunmorl FL conc. (trade name of a soaping agent manufactured by Nicca Chemical Co., Ltd.) | 2 g/l |
| Soda ash | 2 g/l |
| Hydrosulphite | 2 g/l | c) Methods of evaluation (1) Light fastness

The method is the same as in Performance Evaluation Test Example 1.

(2) Measurement of residual ratio

The residual ratio subsequent to HT steaming was measured in the same manner as in Performance Evaluation Test Example 1.

The results are shown in Table 7.

TABLE 7

|  | Light fastness | | Residual ratio (%) |
|---|---|---|---|
|  | A method | B method | subsequent to HT steaming |
| Without addition of aq. disp. of fine particles | 2 | 2 | — |
| Aq. disp. of fine particles in Ex. 1 | 4–5 | 4–5 | 95.7 |
| Aq. disp. of fine particles in Ex. 2 | 4–5 | 4–5 | 96.5 |
| Aq. disp. of fine particles in Ex. 3 | 4–5 | 4–5 | 95.9 |
| Aq. disp. of fine particles in Ex. 4 | 4–5 | 4–5 | 95.5 |
| Aq. disp. of fine particles | 2 | 2 | 62.3 |

TABLE 7-continued

| | Light fastness | | Residual ratio (%) |
| --- | --- | --- | --- |
| | A method | B method | subsequent to HT steaming |
| in Comp. Ex. 1 | | | |
| Aq. disp. of fine particles in Comp. Ex. 2 | 4–5 | 3 | 85.1 |
| Aq. disp. of fine particles in Comp. Ex. 3 | 4 | 4 | 84.6 |
| Aq. disp. of fine particles in Comp. Ex. 4 | 4–5 | 4–5 | 95.2 |
| Aq. disp. of fine particles in Comp. Ex. 5 | 4–5 | 4+ | 94.8 |

Note:
aq. disp. = aqueous dispersion

It is seen from the results that the printed fabrics obtained by the treating agents of the present invention are excellent in light fastness and residual ratio subsequent to HT steaming treatment because of the absence of the sublimation of the treating agents.

Performance Evaluation Test Example 3

Performance evaluation tests were run as described below using the same aqueous dispersions of fine particles as mentioned above.

a) Fabric under test

A seat belt made of a polyester was dyed by a method as described below, and the dyed seat belt was subjected to a light fastness test.

b) Method of treatment

A continuous treating bath as mentioned below was prepared. The seat belt was padded with a mangle at a pickup of about 60%, dried at 100° C. for 1 minute, and treated with a thermosol at 200° C. for 3 minutes using a pin tenter manufactured by Uenoyama Tekko KK. The seat belt was then reduction cleaned in the same manner as in Performance Evaluation Test Example 1.

| Composition of continuous treatment bath | |
| --- | --- |
| C.I. Disperse Yellow 42 | 0.21% by weight |
| C.I. Disperse Red 302 | 0.15% by weight |
| C.I. Disperse Blue 60 | 0.11% by weight |
| Citric acid | 2.00% by weight |
| Sodium arginate | 0.10% by weight |
| Aqueous dispersion of fine particles | 6.00% by weight |
| Water | 91.53% by weight |
| | 100.00% by weight | c) Evaluation methods (1) Light fastness

The light fastness was evaluated in the same manner as in Performance Evaluation Test Example 1.

(2) Measurement of residual ratio

The residual ratio was measured after thermosol treatment in the same manner as in Performance Evaluation Test Example 1.

The results thus obtained are shown in Table 8.

TABLE 8

| | Light fastness | | Residual ratio (%) subsequent |
| --- | --- | --- | --- |
| | A method | B method | to thermosol treatment |
| Without addition of aq. disp. of fine particles | 2 | 2 | — |
| Aq. disp. of fine particles in Ex. 1 | 4–5 | 4–5 | 96.9 |
| Aq. disp. of fine particles in Ex. 2 | 4–5 | 4–5 | 96.0 |
| Aq. disp. of fine particles in Ex. 3 | 4–5 | 4–5 | 96.3 |
| Aq. disp. of fine particles in Ex. 4 | 4–5 | 4–5 | 97.0 |
| Aq. disp. of fine particles in Comp. Ex. 1 | 2 | 2 | 30.8 |
| Aq. disp. of fine particles in Comp. Ex. 2 | 4+ | 3 | 70.5 |
| Aq. disp. of fine particles in Comp. Ex. 3 | 4 | 4– | 67.1 |
| Aq. disp. of fine particles in Comp. Ex. 4 | 4+ | 4 | 96.1 |
| Aq. disp. of fine particles in Comp. Ex. 5 | 4+ | 4 | 93.5 |

Note:
aq. disp. = aqueous dispersion

It is understood from the results that the seat belts treated with the treating agents of the present invention are excellent in residual ratio subsequent to thermosol treatment and in light fastness.

Performance Evaluation Test Example 4

Performance evaluation tests as described below were run using the same aqueous dispersions of fine particles as mentioned above.

a) Fabric under test

A raised polyester fabric (weight: 650 g/m$^2$) for a car sheet was treated as described below, and subjected to a dimming test.

b) Methods of treatment

The fabric was treated at 130° C. for 30 minutes under the conditions as described below using a Minicolor dyeing machine (trade name of a dyeing apparatus manufactured by Tekusamu Giken KK), reduction cleaned at 80° C. for 10 minutes, and dried. The resultant fabric was dry heat treated at 160° C. for 2 minutes using a pin tenter manufactured by Uenoyama Tekko KK, and reduction cleaned by the same procedure as in Performance Evaluation Test Example 1.

| Composition of treatment bath | |
| --- | --- |
| Nicca Sunsolt SD-07 (trade name of a dispersion leveling agent manufactured by Nicca Chemical Co., Ltd.) | 0.5 g/l |
| Acetic acid (90%) | 0.5 g/l |
| Aqueous dispersion of fine particles | 4.0% o.w.f. |
| Liquor to goods ratio | 10:1 | c) Evaluation method

Dimming Test on Windowpane

A circular test sample having a diameter of 70 mm was cut out of the dyed fabric mentioned above, and placed with its raised surface side turned up in a cylindrical glass vessel having a top diameter of 40 mm and a bottom diameter of 70 mm. A transparent glass plate (haze: up to 1%) having a length of 50 mm and a width of 50 mm was placed on the top of the glass vessel, which was heated in an oil bath at 100° C. for 5 hours. The glass plate was then removed, and the dimming thereof was measured using HGM-2DP (direct read type dimming computer manufactured by Suga Shikenki KK). When the read value is smaller, the dimming of the glass plate is lower.

The results thus obtained are shown in Table 9.

TABLE 9

|  | Dimming of glass (%) |
|---|---|
| Without addition of aq. disp. of fine particles | 11.3 |
| Aq. disp. of fine particles in Ex. 1 | 2.8 |
| Aq. disp. of fine particles in Ex. 2 | 2.6 |
| Aq. disp. of fine particles in Ex. 3 | 3.1 |
| Aq. disp. of fine particles in Ex. 4 | 3.5 |
| Aq. disp. of fine particles in Comp. Ex. 1 | 47.3 |
| Aq. disp. of fine particles in Comp. Ex. 2 | 3.1 |
| Aq. disp. of fine particles in Comp. Ex. 3 | 3.7 |
| Aq. disp. of fine particles in Comp. Ex. 4 | 2.9 |
| Aq. disp. of fine particles in Comp. Ex. 5 | 3.5 |

Note:
aq. disp. = aqueous dispersion

It is seen from the results that the fabrics treated with the treating agents of the present invention are excellent in that they exhibit a low dimming.

Performance Evaluation Test Example 5

A performance evaluation test as described below was run using the same aqueous dispersions of fine particles as mentioned above.

a) Fabric under test

A polyester fabric (pongee) was continuously treated as described below, and used in a degradation test.

b) Method of treatment

A continuous treatment bath as described below was prepared. The fabric was padded with a mangle at a pickup of about 80%, dried at 100° C. for 1 minute, treated with a thermosol at 200° C. for 3 minutes using a pin tenter manufactured by Uenoyama Tekko KK, and reduction cleaned in the same manner as in Performance Evaluation Test Example 1.

| Composition of continuous treatment bath | |
|---|---|
| C.I. Disperse Blue 60 | 4.0% by weight |
| Citric acid | 0.2% by weight |
| Sodium arginate | 0.1% by weight |
| Aqueous dispersion of fine particles | 7.0% by weight |
| Water | 88.7% by weight |
| Total | 100.00 by weight | c) Evaluation method

Degradation Test

The treated fabric (backed with a polyurethane 1 cm thick) was subjected to light exposure at 89° C. for 100 hours using a xenon fadeometer manufactured by Suga Shikenki KK, and a measurement of a tear strength was made on the UV-ray-irradiated portion in accordance with JIS L 1018 using Autograph IM-100 (trade name, manufactured by Shimazu Corporation).

Degree of degradation (%)=[(strength of the initial fabric−strength of the fabric under test)/(strength of the initial fabric)]×100

The results are shown in Table 10.

TABLE 10

|  | Degree of degradation of fibers (%) |
|---|---|
| Without addition of aq. disp. of fine particles | 30.7 |
| Aq. disp. of fine particles in Ex. 1 | 12.8 |
| Aq. disp. of fine particles in Ex. 2 | 12.5 |
| Aq. disp. of fine particles in Ex. 3 | 13.4 |
| Aq. disp. of fine particles in Ex. 4 | 12.9 |
| Aq. disp. of fine particles in Comp. Ex. 1 | 24.1 |
| Aq. disp. of fine particles in Comp. Ex. 2 | 16.2 |
| Aq. disp. of fine particles in Comp. Ex. 3 | 18.0 |
| Aq. disp. of fine particles in Comp. Ex. 4 | 14.5 |
| Aq. disp. of fine particles in Comp. Ex. 5 | 13.8 |

Note:
aq. disp. = aqueous dispersion

It is understood from the results that the fabrics treated with the treating agents of the present invention are excellent in that they exhibit a low degree of degradation when exposed to UV radiation.

The treating agents according to the present invention are excellent in adsorption on textile materials, especially cation-dyeable polyester textile materials. Textile materials treated with the agents exhibit improved light fastness and little reduction in strength. Moreover, the treating agents of the invention are excellent in sublimation resistance, and have excellent characteristics that can reduce the dimming of windowpanes, caused by the sublimation in automobiles, etc.

We claim:

1. An agent for treating textile materials, comprising at least one compound selected from the group consisting of compounds of the general formula

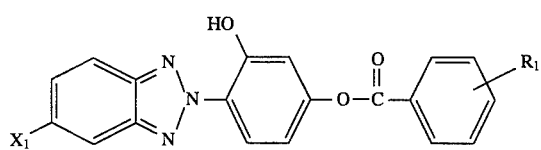

wherein $X_1$ is a hydrogen or halogen and $R_1$ is hydrogen, a halogen or an alkyl of 1 to 4 carbon atoms.

2. An agent as set forth in claim 1 wherein the compound is selected from the group consisting of 2-(2'-hydroxy-4'-benzoyloxyphenyl)-benzotriazole, 2-(2'-hydroxy-4'-p-methylbenzoyloxyphenyl)-benzotriazole, 2-(2'-hydroxy-4'-p-chlorobenzoyloxyphenyl)-benzotriazole, 2-(2'-hydroxy-4'-p-benzoyloxyphenyl)- 5-chlorobenzotriazole, and 2-(2'-hydroxy-4'-p-methylbenzoyloxyphenyl)- 5-chlorobenzotriazole.

3. A compound of the general formula

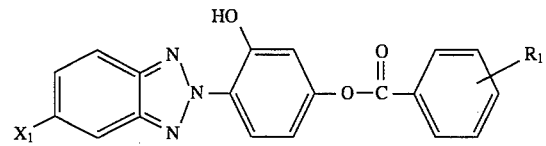

wherein $X_1$ is a hydrogen or halogen and $R_1$ is hydrogen, a halogen or an alkyl of 1 to 4 carbon atoms.

* * * * *